(12) United States Patent
Wendelin et al.

(10) Patent No.: US 10,507,594 B2
(45) Date of Patent: Dec. 17, 2019

(54) PROCESS AND DEVICE FOR INTRODUCING ADDITIVE MATERIALS IN A RECEPTACLE AT THE AREA OF HIGHEST PRESSURE

(71) Applicant: EREMA Engineering Recycling Maschinen und Anlagen Gesellschaft m.b.H., Ansfelden (AT)

(72) Inventors: Gerhard Wendelin, Linz (AT); Klaus Feichtinger, Linz (AT); Manfred Hackl, Ansfelden (AT)

(73) Assignee: EREMA ENGINEERING RECYCLING MASCHINEN UND ANLAGEN GESELLSCHAFT M.B.H., Ansfelden (AT)

( * ) Notice: Subject to any disclaimer, the term of this patent is extended or adjusted under 35 U.S.C. 154(b) by 175 days.

(21) Appl. No.: 14/845,221

(22) Filed: Sep. 3, 2015

(65) Prior Publication Data
US 2016/0101540 A1 Apr. 14, 2016
US 2017/0008194 A9 Jan. 12, 2017

Related U.S. Application Data

(63) Continuation of application No. 12/516,177, filed as application No. PCT/AT2007/000527 on Nov. 22, 2007, now abandoned.

(30) Foreign Application Priority Data

Nov. 23, 2006 (AT) .................................. 1951/2006

(51) Int. Cl.
  B29B 7/42 (2006.01)
  B01F 7/16 (2006.01)
  (Continued)

(52) U.S. Cl.
  CPC ............ *B29B 7/42* (2013.01); *A61B 5/04001* (2013.01); *A61B 5/685* (2013.01); *A61N 1/0529* (2013.01);
  (Continued)

(58) Field of Classification Search
  CPC .......... B01F 7/162; B01F 3/1221; B01F 3/14; B01F 7/163; B01F 15/0203; B29B 7/42;
  (Continued)

(56) References Cited

U.S. PATENT DOCUMENTS 735,987 A * 8/1903 Kleinschmidt et al. .. C11B 1/12
165/109.1
973,324 A * 10/1910 Wannenwetsch ......... C11B 1/12
137/587
(Continued)

FOREIGN PATENT DOCUMENTS

GB 728323 * 4/1955
GB 834007 * 5/1960
(Continued)

OTHER PUBLICATIONS

A.C. Hoogerwerf and K.D. Wise, "A three-dimensional microelectrode array for chronic neural recording," IEEE Transactions on Biomedical Engineering, vol. 41, No. 12, pp. 1136-1146, Dec. 1994.
(Continued)

*Primary Examiner* — Charles Cooley
(74) *Attorney, Agent, or Firm* — Kilpatrick Townsend & Stockton LLP

(57) ABSTRACT

A method and a device for introducing and/or adding non-dry-powder additive materials and/or coating materials with a liquid, solid, semi-solid, or paste-like consistency or in suspended or emulsified form, for example, peroxides, fats, waxes, IV improvers, polymers, or similar materials, to an existing lumpy or particulate material which is moved
(Continued)

and mixed, and optionally warmed and reduced to small pieces in a receptacle and/or compressor, said material being in particular polymer particles and/or flakes, wood fibers, paper cuttings, or similar materials. According to the invention, the additive material is introduced below the level of the material and/or material particles already in the receptacle.

20 Claims, 1 Drawing Sheet

(51) Int. Cl.
    *B01F 3/14*     (2006.01)
    *B01F 15/02*     (2006.01)
    *B02C 18/12*     (2006.01)
    *B02C 18/22*     (2006.01)
    *B29B 7/60*     (2006.01)
    *B29B 7/88*     (2006.01)
    *B29B 17/04*     (2006.01)
    *A61N 1/05*     (2006.01)
    *B29B 7/94*     (2006.01)
    *B29C 48/285*     (2019.01)
    *A61B 5/04*     (2006.01)
    *A61B 5/00*     (2006.01)
    *B01F 3/12*     (2006.01)
    *B29C 48/04*     (2019.01)
    *B29K 105/00*     (2006.01)
    *B29K 105/06*     (2006.01)
    *B29C 48/08*     (2019.01)
    *B29C 48/29*     (2019.01)

(52) U.S. Cl.
    CPC .............. *B01F 3/1221* (2013.01); *B01F 3/14* (2013.01); *B01F 7/162* (2013.01); *B01F 7/163* (2013.01); *B01F 15/0203* (2013.01); *B02C 18/12* (2013.01); *B02C 18/2225* (2013.01); *B29B 7/603* (2013.01); *B29B 7/88* (2013.01); *B29B 7/94* (2013.01); *B29C 48/2886* (2019.02); *A61B 2562/046* (2013.01); *A61N 1/0536* (2013.01); *A61N 1/0551* (2013.01); *B29B 17/0412* (2013.01); *B29B 2017/048* (2013.01); *B29C 48/04* (2019.02); *B29C 48/08* (2019.02); *B29C 48/288* (2019.02); *B29C 48/29* (2019.02); *B29K 2105/0005* (2013.01); *B29K 2105/06* (2013.01); *Y02W 30/625* (2015.05)

(58) Field of Classification Search
    CPC .. B29B 7/603; B29B 7/88; B29B 7/94; B29B 2017/048; B29B 17/0412; B02C 18/12; B02C 18/2225; A61B 5/04001; A61B 5/685; A61B 2562/046; A61B 2562/0209; A61N 1/0529; A61N 1/0551; A61N 1/0536; B29C 47/1045; B29C 47/1027; B29C 47/1063; B29C 47/0021; B29C 47/0011; Y02W 30/625; B29K 2105/06; B29K 2105/0005
    USPC ...... 366/76.2, 76.4, 76.6, 76.9–76.93, 154.1, 366/155.1, 156.1, 158.4, 79–91, 147, 366/76.3, 168.1, 172.1, 172.2, 149, 182.1, 366/314; 425/586–587
See application file for complete search history.

(56) References Cited

U.S. PATENT DOCUMENTS

| | | | | |
|---|---|---|---|---|
| 1,111,408 A | * | 9/1914 | Schneible | D06B 13/00 366/265 |
| 1,160,217 A | * | 11/1915 | Valerius | B01F 7/007 165/72 |
| 3,024,010 A | * | 3/1962 | Sperling | B01F 7/162 241/282.1 |
| 3,250,519 A | * | 5/1966 | Herfeld | B01F 7/162 261/130 |
| 3,410,530 A | * | 11/1968 | Gilman | B01F 3/18 222/63 |
| 3,430,925 A | * | 3/1969 | Buhner | B01F 3/088 241/282.1 |
| 3,664,641 A | * | 5/1972 | Morin | B01F 5/26 222/135 |
| 3,797,702 A | * | 3/1974 | Robertson | B01F 7/00208 198/526 |
| 3,799,510 A | * | 3/1974 | Schott, Jr. | B29B 17/0005 366/147 |
| 3,861,287 A | * | 1/1975 | Manser | A23N 17/005 366/147 |
| 3,871,629 A | * | 3/1975 | Hishida | B29C 45/1816 198/526 |
| 3,998,439 A | * | 12/1976 | Feix | B29C 45/1816 222/240 |
| 4,014,462 A | * | 3/1977 | Robertson | B01F 7/00208 222/136 |
| 4,019,722 A | * | 4/1977 | Shohet | B01F 7/166 366/261 |
| 4,039,168 A | * | 8/1977 | Caris | B30B 11/24 366/147 |
| 4,148,100 A | * | 4/1979 | Moller | B29C 47/1009 366/156.1 |
| 4,155,657 A | * | 5/1979 | King | B01F 3/0807 366/160.1 |
| 4,222,728 A | * | 9/1980 | Bacher | B29B 17/0412 241/101.2 |
| 4,334,784 A | * | 6/1982 | Engels | B01F 15/0429 222/135 |
| 4,344,579 A | * | 8/1982 | Morita | B02C 13/28 241/101.6 |
| 4,353,851 A | * | 10/1982 | Godfrey | B29B 17/0005 264/140 |
| 4,378,897 A | * | 4/1983 | Kattelmann | B65D 90/48 198/316.1 |
| 4,443,109 A | * | 4/1984 | Watts | B01F 5/241 222/132 |
| 4,460,277 A | * | 7/1984 | Schulz | B29B 7/7461 241/101.2 |
| 4,467,969 A | * | 8/1984 | Godfrey | B29B 17/0005 241/101.4 |
| 4,486,100 A | * | 12/1984 | Endo | B29C 47/92 222/71 |
| 4,636,085 A | * | 1/1987 | Kopernicky | B29B 7/847 366/139 |
| 4,728,475 A | * | 3/1988 | Beck | D01F 1/06 264/177.2 |
| 4,728,476 A | * | 3/1988 | Boring | B29C 45/0013 264/328.18 |
| 4,746,478 A | * | 5/1988 | Fujisaki | B29C 44/3442 264/53 |
| 4,955,550 A | * | 9/1990 | Satake | B01F 15/0445 222/14 |
| 5,078,163 A | * | 1/1992 | Holley | B01D 53/74 118/417 |
| 5,100,239 A | * | 3/1992 | Ono | B28C 5/468 366/108 |
| 5,102,326 A | * | 4/1992 | Bacher | B29B 13/10 264/918 |
| 5,127,450 A | * | 7/1992 | Saatkamp | B29B 17/0005 141/105 |
| 5,213,724 A | * | 5/1993 | Saatkamp | B29C 31/06 264/37.32 |

(56) References Cited

U.S. PATENT DOCUMENTS

| | | | | |
|---|---|---|---|---|
| 5,225,137 A * | 7/1993 | Sadr | B29B 17/02 | 241/23 |
| 5,261,743 A * | 11/1993 | Moller | B29B 7/728 | 177/121 |
| 5,282,548 A * | 2/1994 | Ishihara | B29C 31/02 | 222/55 |
| 5,451,106 A * | 9/1995 | Nguyen | B01F 5/0663 | 138/42 |
| 5,458,474 A * | 10/1995 | Neubauer | B29B 9/06 | 366/91 |
| 5,511,877 A * | 4/1996 | King | B01F 7/00816 | 366/169.2 |
| 5,536,154 A * | 7/1996 | Bacher | B29B 13/10 | 241/101.2 |
| 5,653,534 A * | 8/1997 | Matsumoto | B29C 45/1816 | 366/76.1 |
| 5,660,466 A * | 8/1997 | Hopson | B01F 5/205 | 239/113 |
| 5,683,632 A * | 11/1997 | Shimizu | B29B 7/244 | 264/349 |
| 5,718,508 A * | 2/1998 | Williams | B01F 7/00433 | 366/138 |
| 5,772,319 A * | 6/1998 | Pemberton | B29C 31/02 | 222/159 |
| 5,783,225 A * | 7/1998 | Bacher | B29B 17/04 | 366/76.1 |
| 5,816,700 A * | 10/1998 | Starke, Sr. | D01D 1/065 | 264/319 |
| 5,860,737 A * | 1/1999 | Hauser | B01F 3/1271 | 366/139 |
| 5,882,558 A * | 3/1999 | Bacher | B29B 17/0005 | 264/102 |
| 5,988,865 A * | 11/1999 | Bacher | B29B 17/04 | 366/76.93 |
| 6,334,856 B1 | 1/2002 | Allen et al. | | |
| 6,474,972 B1 * | 11/2002 | Endo | B29B 9/06 | 366/141 |
| 6,619,575 B1 * | 9/2003 | Bacher | B29B 17/0412 | 241/154 |
| 6,719,454 B1 * | 4/2004 | Bacher | B02C 13/16 | 241/186.5 |
| 6,784,214 B1 * | 8/2004 | Bacher | B29B 13/06 | 521/48 |
| 6,883,953 B1 * | 4/2005 | Bacher | B29B 17/0026 | 241/186.5 |
| 7,108,500 B2 * | 9/2006 | Bacher | B29B 13/06 | 264/37.1 |
| 7,137,802 B2 * | 11/2006 | Bacher | B29B 17/0412 | 264/140 |
| 7,169,340 B2 * | 1/2007 | Hawley | B29B 15/122 | 264/136 |
| 7,275,703 B2 * | 10/2007 | Bacher | B29B 13/10 | 241/152.2 |
| 7,275,857 B2 * | 10/2007 | Bacher | B01F 7/00466 | 366/314 |
| 7,291,001 B2 * | 11/2007 | Bacher | B01F 7/163 | 241/186.5 |
| 7,309,224 B2 * | 12/2007 | Bacher | B29B 13/10 | 241/186.5 |
| 7,404,665 B2 * | 7/2008 | Bacher | B29B 17/0036 | 366/154.1 |
| 7,431,583 B2 * | 10/2008 | Takatsugi | B29C 45/18 | 366/76.2 |
| 7,585,102 B2 * | 9/2009 | Bacher | B29B 17/0036 | 366/147 |
| 7,690,834 B2 * | 4/2010 | Nakamura | B01F 7/00766 | 156/39 |
| 7,842,221 B2 * | 11/2010 | Magni | B29B 7/7461 | 241/277 |
| 8,123,394 B2 * | 2/2012 | Becht | B01F 3/10 | 366/138 |
| 8,399,599 B2 * | 3/2013 | Hackl | B29B 13/10 | 422/134 |
| 8,419,997 B2 * | 4/2013 | Hackl | B29B 13/10 | 264/328.17 |
| 8,616,478 B2 * | 12/2013 | Weigerstorfer | B01F 7/163 | 241/186.5 |
| 8,835,594 B2 * | 9/2014 | Hackl | B29B 13/10 | 422/134 |
| 9,808,963 B2 * | 11/2017 | Feichtinger | B29B 17/0036 | |
| 9,821,492 B2 * | 11/2017 | Feichtinger | B29B 17/0036 | |
| 10,173,346 B2 * | 1/2019 | Weigerstorfer | B29B 17/0412 | |
| 2001/0024400 A1 * | 9/2001 | Van Der Wel | B01F 7/00208 | 366/143 |
| 2002/0036948 A1 * | 3/2002 | Yamaguchi | B28B 3/22 | 366/76.3 |
| 2002/0079607 A1 * | 6/2002 | Hawley | B29C 45/1816 | 264/136 |
| 2004/0006264 A1 | 1/2004 | Mojarradi et al. | | |
| 2004/0202744 A1 * | 10/2004 | Bacher | B29B 17/0036 | 425/207 |
| 2004/0219247 A1 * | 11/2004 | Bacher | B29B 13/06 | 425/215 |
| 2005/0170029 A1 * | 8/2005 | Bacher | B01F 7/00466 | 425/6 |
| 2005/0287237 A1 * | 12/2005 | Bacher | B29B 17/0412 | 425/217 |
| 2006/0093696 A1 * | 5/2006 | Bacher | B01F 7/163 | 425/200 |
| 2006/0292259 A1 * | 12/2006 | Bacher | B29B 13/10 | 425/217 |
| 2007/0007240 A1 | 1/2007 | Wise et al. | | |
| 2007/0007375 A1 * | 1/2007 | Bacher | B29B 13/10 | 241/199.12 |
| 2007/0026096 A1 * | 2/2007 | Takatsugi | B29C 45/18 | 425/147 |
| 2008/0273417 A1 * | 11/2008 | Bacher | B29B 17/0036 | 366/76.2 |
| 2008/0290537 A1 * | 11/2008 | Bacher | B01F 7/18 | 264/37.1 |
| 2009/0004325 A1 * | 1/2009 | Bacher | B29B 17/0026 | 425/586 |
| 2010/0101454 A1 * | 4/2010 | Wendelin | B01F 3/1221 | 106/243 |
| 2010/0140381 A1 * | 6/2010 | Weigerstorfer | B01F 7/163 | 241/17 |
| 2011/0049763 A1 * | 3/2011 | Hackl | B29B 13/10 | 264/328.17 |
| 2011/0251368 A1 * | 10/2011 | Hackl | B29B 13/10 | 526/352 |
| 2012/0091609 A1 * | 4/2012 | Feichtinger | B29B 17/0026 | 264/37.31 |
| 2013/0087641 A1 * | 4/2013 | Hackl | B29B 17/0412 | 241/15 |
| 2013/0092768 A1 * | 4/2013 | Feichtinger | B29B 17/02 | 241/20 |
| 2013/0113139 A1 * | 5/2013 | Weigerstorfer | B29B 17/0412 | 264/340 |
| 2013/0168201 A1 * | 7/2013 | Hackl | B29B 13/10 | 193/2 R |
| 2014/0234461 A1 * | 8/2014 | Feichtinger | B01F 15/0289 | 425/202 |
| 2014/0234462 A1 * | 8/2014 | Feichtinger | B01F 15/0289 | 425/202 |
| 2014/0239104 A1 * | 8/2014 | Feichtinger | B01F 15/0289 | 241/188.1 |
| 2014/0248388 A1 * | 9/2014 | Feichtinger | B01F 15/0289 | 425/203 |
| 2014/0252147 A1 * | 9/2014 | Feichtinger | B01F 15/0289 | 241/86 |
| 2014/0252148 A1 * | 9/2014 | Feichtinger | B01F 15/0289 | 241/86 |
| 2014/0271968 A1 * | 9/2014 | Feichtinger | B01F 15/0289 | 425/202 |
| 2014/0287081 A1 * | 9/2014 | Feichtinger | B01F 15/0289 | 425/202 |

(56) References Cited

U.S. PATENT DOCUMENTS

| | | | | |
|---|---|---|---|---|
| 2014/0291427 A1* | 10/2014 | Feichtinger | ......... | B01F 15/0289 241/101.2 |
| 2014/0295016 A1* | 10/2014 | Feichtinger | ......... | B01F 15/0289 425/202 |
| 2014/0299700 A1* | 10/2014 | Feichtinger | ......... | B01F 15/0289 241/101.2 |
| 2014/0312151 A1* | 10/2014 | Feichtinger | ......... | B01F 15/0289 241/101.2 |
| 2016/0101540 A1* | 4/2016 | Wendelin | ........... | A61B 5/04001 241/245 |
| 2019/0126512 A1* | 5/2019 | Gribaudo | ............ | B29C 45/0441 |

FOREIGN PATENT DOCUMENTS

| | | | |
|---|---|---|---|
| WO | 89/07042 | * | 8/1989 |
| WO | 93/22119 | * | 11/1993 |

OTHER PUBLICATIONS

A.M. Sodager, G.E. Perlin, Y. Yao, K.D. Wise, and K. Najafi, "An implantable microsystem for wireless multi-channel cortical recording," in Proc. of the Solid State Sensors, Actuators, and Microsystems Conference (Transducers), 2007, pp. 69-72.

B. Humphrey, "Using parylene for medical substrate coating," Medical plastics and Biomaterials, p. 28, Jan. 1996.

C. Kim and K.D. Wise, "A 64-site multishank CMOS low-profile neural stimulating probe," IEEE Journal of Solid-States Circuits, vol. 31, No. 9, pp. 1230-1238, Sep. 1996.

D.F. Lemmerhirt and K.D. Wise, "Air-isolated through-wafer interconnects for microsystem applications," Proceedings of the Solid-State Sensors, Actuators, and Microsystems (TRANSDUCERS), 2003, pp. 1067-1070.

E.M. Schmidt, J.S. Mcintosh and M.J. Bak, "Long-term implants of parylene-C coated microelectrodes," Med. Biol. Eng. Comp., vol. 26, 1988, pp. 96-101.

G.E. Loeb, M.J. Bak, M. Salcman and E.M. Schmidt, "Parylene as a chronically stable, reproducible microelectrode insulator," IEEE Trans. Biomed. Eng., vol. 24, 1977, pp. 121-128.

G. Phipps, "Wire bond vs. flip chip packaging: a technical trade-off analysis," Advanced Packaging, vol. 14, No. 7, Jul. 2005.

I.W. Qin, "Wire bonding tutorial: advances in bonding technology," Advanced Packaging, vol. 14, No. 7, Jul. 2005.

J.-M. Hsu, S. Kammer, E. Jung, L. Rieth, R.A. Normann, and F. Solzbacher, "Characterization of Parylene-C film as an encapsulation material for neural interface devices," Proc. of the Conference on Multi-Material Micro Manufacture, Oct. 2007, pp. 16-23.

K. Najafi, "Solid state microsensors for cortical nerve recordings," IEEE Engineering in Medicine & Biology, pp. 375-387, Jun./Jul. 1994.

K. Najafi, J. Ji, and K.D. Wise, "Scaling limitations of silicon multichannel recording probes," IEEE Transactions on Biomedical Engineering, vol. 37, No. 1, pp. 1-11, Jan. 1990.

L. Wolgemuth, "Assessing the performance and suitability of parylene coating," Medical Device and Diagnostic Industry, vol. 22, 2000, p. 42-49.

M. Topper et al., "Biocompatible hybrid flip chip microsystem—integration for next generation wireless neural interfaces," In Proc. of the Electronic Components and Technology Conference (ECTC), 2006, pp. 705-708.

P. Rousche, D.S. Pellinen, D.P. Pivin, J.C. Williams, R.J. Veter, and D.R. Kipke, "Flexible polyimide-based intracortical electrode arrays with bioactive capability," IEEE Transactions on Biomedical Engineering, vol. 48, No. 3, pp. 361-370, Mar. 2001.

P.T. Bhatti and K.D. Wise, "A 32-site 4-channel high density electrode array for a cochlear prosthesis," IEEE Journal of Solid-State Circuits, vol. 41, No. 12, pp. 2965-2973, Dec. 2006.

P.K. Campbell, K.E. Jones, R.J. Huber, K.W. Horch, and R.A. Normann, "A silicon-based, three-dimensional neural interface: manufacturing processes for an intracortical electrode array," IEEE Transactions on Biomedical Engineering, vol. 38, No. 8, pp. 758-766, Aug. 1991.

Q. Bai, K.D. Wise, J.F. Hetke, and D.J. Anderson, "A microassembly structure for intracortical three-dimensional electrode arrays," in Proceedings of the 18$^{th}$ Annual International Conference of the IEEE Engineering in Medicine and Biology Society (EMBC), 1996, pp. 264-265.

S. Kim, M. Wilke, M. Klein, M. topper, and F. Solzbacher, "Electromagnetic compatibility of two novel packaging concepts of an inductively powered neural interface," in Proc. of the IEEE/EMBS Conference on Neural Engineering, 2007, pp. 434-437.

S. Takeuchi, T. Suzuki, K. Mabuchi, and H. Fujita, "3D flexible multichannel neural probe array," Journal of Micromechanical Microengineering, vol. 14, pp. 104-107, 2004.

Y. Yao, M.N. Gulari, J.F. Hetke, and K.D. Wise, "A low-profile three-dimensional neural stimulating array with on-chip current generation," in Proceedings of the 26$^{th}$ Annual International Conference of the IEEE Engineering in Medicine and Biology Society (EMBC), 2004, pp. 1994-1997.

A.M. Sodagar, G.E. Perlin, Y. Yao, K.D. Wise, and K. Najafi, "An implantable microsystem for wireless multi-channel cortical recording," in Proc. of the Solid State Sensors, Actuators, and Microsystems Conference (Transducers), 2007, pp. 69-72.

Gaiser Tool Company, Publications: Single Point T.A.B., pp. 133-145.

P. Rousche, D.S. Pellinen, D.P. Pivin, J.C. Williams, R.J. Vetter, and D.R. Kipke, "Flexible polyimide-based intracortical electrode arrays with bioactive capability," IEEE Transactions on Biomedical Engineering, vol. 48, No. 3, pp. 361-370, Mar. 2001.

Non-Final Office Action dated Nov. 28, 2011, for U.S. Appl. No. 12/415,177, 13 pages.

* cited by examiner

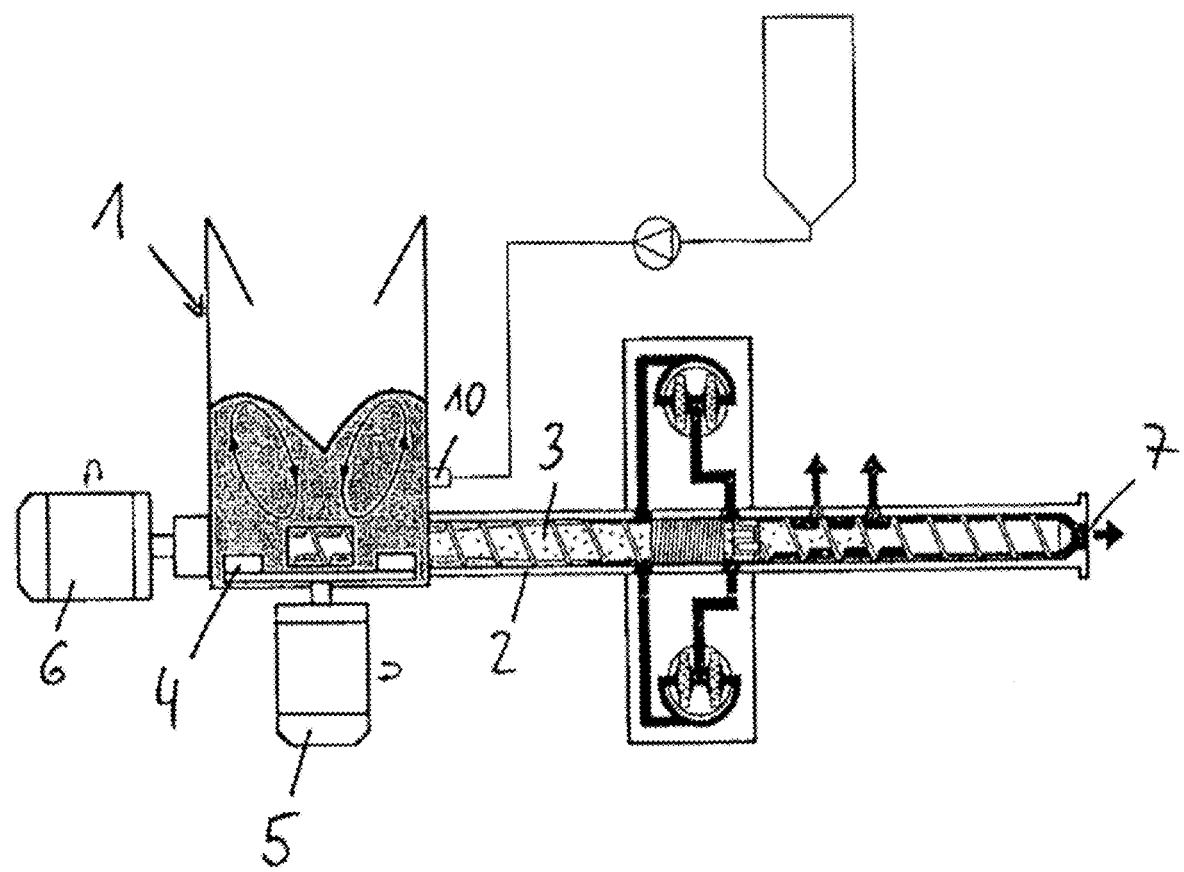

PROCESS AND DEVICE FOR INTRODUCING ADDITIVE MATERIALS IN A RECEPTACLE AT THE AREA OF HIGHEST PRESSURE

CROSS-REFERENCES TO RELATED APPLICATIONS

This application is a continuation of U.S. application Ser. No. 12/516,177, filed Jan. 12, 2010, which is a National Stage of International Application No. PCT/AT2007/000527 filed Nov. 22, 2007, which claims priority to Austrian Patent Application No. A 1951/2006, filed Nov. 23, 2006, the disclosures of all applications being incorporated herein by reference.

BACKGROUND OF THE INVENTION

The invention relates to a process according to a method for introducing and adding a non-dry particulate to a material and a device for introducing and adding a non-dry particulate to a material.

Numerous processes and devices are known from the prior art in which the liquid additives are either sprayed from above onto the plastic material or added in the fluid bed process.

It is known from U.S. Pat. No. 4,522,957 to add liquid additives to plastic granules in a mixer.

In WO 00/38895, to reduce the dust nuisance or dust formation, a process of this type is further improved, in a first step, by spraying the liquid additives onto the plastic granules in a spray chamber in the countercurrent process, followed by a static mixing process.

In EP 7624, a liquid additive is added to the plastic granules, namely in an inert gas current.

In WO 84/02530, the plastic granules are first whirled in a continuous mixer and, in this turbulent state, wetted with a highly heated liquid additive in the gas stream.

A process is known from WO 9425509 in which polymer granules are wetted in a mixing device with a liquid additive via an injection nozzle, whereby, to improve the wetting, the surface of the plastic granules is structured irregularly or is roughened.

A process and a mixing device are described in WO 2006/010291 in which a liquid additive is added to plastic granules via an injection device in a mixer and the mixture subsequently reaches an extruder.

Furthermore, a process is known from EP 9817 in which the plastic granules are first wetted with a "coupling agent" or carrier which is to ensure better distribution of the liquid additive on the surface of the plastic granules. In particular, paraffins or paraffin-like substances are noted as coupling agents.

Furthermore, a process is known from U.S. Pat. No. 4,703,093 in which a liquid additive is added to already preheated plastic granules.

DE 263 16 22 describes a process for the simultaneous and continuous feeding of powdery solids and liquids in treatment machines. This occurs via a ring nozzle, wherein the liquid is formed into a tubular casing in the centre of which the solids are introduced.

However, processes of this type are primarily suitable only for highly fluid, finely sprayable additives and function only inadequately for highly viscous, sluggish additives or for additives of solid or semi-solid consistency. In most cases, the plastic material is only wetted incompletely and unevenly.

If highly viscous additives are heated to higher temperatures in order to enable them to be added nevertheless in a highly fluid form, then deposits or precipitates of the additives are often formed at cooler points or colder surfaces of the device.

This leads to difficulties and inaccuracies during dosing and to contamination of the devices.

BRIEF SUMMARY OF THE INVENTION

The object of the invention is to create a process and a device by means of which the non-dry particle-like, highly viscous additives can be easily and uniformly added to a given fragmented material, in particular a plastic material or polymer particles. The surface of the material should thereby be wetted as completely and uniformly as possible with the additives and the additives should be uniformly distributed or dispersed within the material particles. Moreover, the additives should be added in correct dosages and be able to prevent deposits and thus contaminations at undesired points.

These objects are solved by the characterizing features of the disclosed embodiments.

The process of the invention or the device of the invention make it possible to very uniformly and homogeneously advantageously apply additives or coating substances to fragmented, particle-like materials, so that a complete wetting of the surface of the material particles results.

Moreover, in this way, the smallest amounts of additives can also be accurately dosed, since the entire amount of the additives used are introduced directly into the material particles and there is no possibility for the additives to be deposited. In particular, this is ensured by the fact that the additives do not come into contact with any colder components of the container or reactor. This does not result in any contaminations whatsoever or material deposits of condensed or solidifed additives at undesirable points in the reactor, as a result of which frequent cleaning is no longer required. The precipitation of additives or dust with additives at cooler points is greatly reduced or even prevented in comparison to the introduction by spraying the additives onto the material particles from above, which is known from the prior art.

The dynamic movement or rotation of the material particles in the container facilitates the introduction of the additives, the application onto the surfaces of the material particles and promotes the uniform distribution or dispersion of the additives on the material particles. This is ensured thereby that the material particles glide along or rotate past on the inside of the side wall of the container and, in this way, take or carry along the additives flowing out there.

Thus, by means of the process according to the invention, the entire surface is wetted and the additives optimally distributed in the mixture of the particles.

One or more feeding devices can be provided. These feeding devices are arranged on the inside of the side wall of the container or lead into the container on the inside of the side wall of the container.

There are various possibilites for attaching and placing the feeding devices. It is especially advantageous to provide several feeding devices which are, for example, arranged at the same level above the container bottom or mixing tool and are preferably uniformly distributed over the periphery of the inner wall of the container.

A further possibility is to arrange the individual feeding devices in a straight vertical row or a diagonally upward extending row above one another, optionally offset or in the form of a spiral. The feeding devices may also be, in particular, statistically or uniformly distributed, or only a single feeding device can be provided.

The feeding devices are arranged in the container in such a way that they are, in particular, continuously and permanently situated below the level of the material found in the container, so that the additives can be exclusively added directly into the quantity of the rotating material particles. In most cases, a mixing vortex is formed due to the movement of the material particles inside the container, which is also schematically shown in The FIGURE. Advantageously, the edge or the uppermost level of the mixing vortex should be located above the feeding devices during the entire process.

Advantageously, the feeding devices are arranged at the level of the middle third area of the fill level of the material in the container or the mixing vortex, as a result of which the additives are uniformly disperse on the material particles.

In particular for very highly viscous additives, it is advantageous if the feeding devices are arranged in that area or at that level of the inside of the container at which the moved or rotating material particles exert the highest pressure. As a result, a good distribution of the material is ensured. This area or the pressure exerted by the material on the side wall is determined in dependency on the rotational speed, the type, number and form of the mixing tool.

The feeding devices can be formed as simple feed connections or feed openings in the side wall of the container or also be designed in the form of feed nozzles. The additives are preferably dosed or supplied via dosing pumps, e.g. gear pumps or diaphragm pumps. These control the amount of the additives added. Since, as described, all of the additives can be introduced directly into the material particles, they can be dosed very accurately and free of loss. Losses due to deposits or the like are largely excluded.

In order not to disturb the movement of the material particles inside the container, it is advantageous if the feeding devices are sealed flush with the inner wall of the container and do not project or protrude inside the container.

Usually, the additive which is to be introduced into the material emerges from the feeding devices in the form of droplets or in pasty form. As a result of the movement forced by the mixing tool, the material particles move along the inner wall of the container, come into contact with it and rub against it. Consequently, the additives just emerging through the feeding device are immediately and directly carried along by the material particles and are distributed all the better in the mixture.

For some additives, a wetting of the container wall by the additives may be desirable in order to consequently produce a better dispersion of the additives with the material particles. To enable this, an additional separate heating device can be provided which merely heats the inside of the side wall of the container or the container side wall. This heating device is advantageously independent of temperable or heatable mixing tools or further heating devices for heating the material in the container. In this way, the viscosity of the additives is reduced, as a result of which the flowability of the additives is improved and the inner wall of the container is better wetted. Consequently, an even better distribution of the additives is given on the material particles.

To prevent obstructions of pasty or highly viscous additives, the feeding devices themselves and their feed lines or storage tanks may also be heatable. In this way, solid or pasty waxes can be added in sufficiently fluidized form, e.g. at room temperature. If necessary, the pressure which is exerted on the additives or with which the additives are supplied can also be adjusted accordingly, in particular selected at a corresponding level, in order to be able to introduce highly viscous additives.

Basically, it is advantageous to treat the material at an increased temperature or rather to maintain the temperature of the material higher, since the viscosities of the additives are lowered as a result and a better distribution and homogeneous dispersion of the material particles take place.

Furthermore, it can be advantageous to avoid or reduce a wetting of the inner wall of the container by the additives. This can be accomplished, for example, by special coatings or also by special embossings of the container wall. In this way, the additive droplets adhering to the inner wall of the container can better loosen from the side wall and be more easily carried along by the material or by the moving material particles and a wetting of the container wall is omitted.

Further advantages and embodiments of the invention can be found in the description and the attached drawing.

The invention is schematically illustrated with reference to embodiments in the drawing and is described by way of example in the following with reference to the drawing.

BRIEF DESCRIPTION OF THE DRAWINGS

The FIGURE shows a schematic view of a device according to the invention.

DETAILED DESCRIPTION OF THE PREFERRED EMBODIMENTS

A device according to the invention is shown in a schematic sectional view in The FIGURE.

The device in the form of a cutting compacter shown in The FIGURE has a receptacle 1 in the bottom area of which a crushing or mixing tool 4 that is pivotable about a vertical axis is provided which is actuated by a drive motor 5. At the level of this crushing and mixing tool 4, an opening is provided in the side wall of the receptacle 1 to which the housing 2 of a screw extruder is attached. An extruder screw 3 which is actuated by a drive motor 6 is located in the housing 2. The crushed and mixed material, in particular a plastic material, conveyed by the screw extruder emerges from the screw housing through the outlets 7. When plastic material is processed, the material is first melted or plasticized in the extruder. The container 1 may also be acted upon with a vacuum.

The material to be treated is given in the receptacle 1. The material is present in the receptacle 1 in a fragmented or particle-like form and thus has a large surface in relation to its volume. The material can be, for example, thermoplastic material in the form of flakes, granules, foil waste or the like. Wood fibres, newsprint paper or the like are also feasible. Due to the continuous dynamic movement or rotation of the material particles in the receptacle 1 caused by the mixing tool 4, the individual particles are thoroughly mixed and, optionally, depending on the configuration of the mixing tool 4, the material is also crushed and/or precompacted and perhaps also heated or dried or crystallized. The movement of the material particles in the receptacle 1 serves, in particular with plastic materials, to ensure that the individual plastic particles do not stick together when heated and that the fragmented character of the material remains intact.

Furthermore, a feeding device 10 in the form of a feed connection is provided in the lower area of the side wall of the container 1, which opens into the container 1 via an opening, whereby the opening seals flush with the inner surface of the side wall and no part of the feeding device 10 protrudes inside the container. One or more additives or coating substances can be dosed into the receptacle 1 via this feeding device 10.

The feeding device 10 is configured such that it is suitable for feeding non-dry particle-shaped or non-dry powdery or non-dry granular or non-dry crystalline additives. Dry powdery or granular additives, e.g. pigments, fillers or the like, are for the most part added from the top via a simple feed funnel. Thus, pumpable highly fluid or viscous, solid, semi-solid or pasty additives, in particular of higher viscosity, are added via the feeding device 10. For example, the feeding device 10 is suitable for adding highly fluid additives, such as plasticizers, peroxides, etc., viscous additives or also pasty, or more solid additives having a cream-like or pasty consistency, e.g. fats or waxes or also polymers. The term solid additives refers, for example, to waxes or fats which are inherently stable at room temperature, but nevertheless are still ductile and moldable. Originally, powdery additives or aggregates, such as pigments, fillers or the like, can also be added in this way by means of a carrier solution as dispersion or suspension, perhaps also as a suspension or emulsion.

According to the FIGURE, the feeding device 10 is placed below the level of the rotating material particles found in the container 1 or below the uppermost edges of the mixing vortex. Additives are therefore not added from the top, for example by spraying or drop by drop, but through the side wall of the container 1. The feeding device 10 or the feed opening is thereby always brushed over by material that moves past and the emerging additives are carried along and in this way applied to the material particles and dispersed or distributed within the material particles. As is clearly seen in the FIGURE, the feeding device 10 is displaced vertically above the upper edge of the mixing tool 4 such that a vertical gap is present between the feeding device 10 and the mixing tool upper edge.

The dispersion of the additives functions all the better, the larger the surfaces of the material particles are.

The additives, in particular reactive additives, are added, depending on the degree of dilution, through an eventual carrier of the additives, in amounts of between 0.01 and 20% by weight. For example, when using PET flakes as receiver material, a quantity of 0.2 to 0.6% of an additive is applied.

The maximum amount with which the additives are to be used is that amount which is necessary to wet the entire surface of the material found in the container 1 or the entire surface of the material particles.

Depending on the type of additive used and its reactivity, a reaction of the additive with the material perhaps does not take place until in the extruder or in the molten mass.

Finally, the material is completely melted in the extruder and, if necessary, filtered and/or degassed.

The process according to the invention can be carried out in one step, but can also be included in a two or more step process. Advantageously, the additives are thereby already added in the first step, in a pretreatment container connected upstream or in a first receptacle 1. For this purpose, the feeding devices are arranged in this pretreatment container. The further treatment of the material and/or the addition of further additives or an eventual drying or crystallizing then takes place in further containers 1.

What is claimed is:

1. A method for feeding non-dry particulate, additives or coating stuffs to a material, the method comprising:
   providing a receptacle having a lateral wall;
   charging the receptacle with the material to a charging level;
   providing at least one mixing tool of a predetermined shape within the receptacle;
   rotating the mixing tool at a rotational speed wherein the speed and shape of the mixing tool moves or rotates the material in the receptacle thereby generating a region on the lateral wall at which the moving or rotating material exerts a highest pressure;
   providing the receptacle with at least one feeding device located on the lateral wall at the region of highest pressure;
   feeding the non-dry particulate, additives or coating stuffs into the receptacle at the region of highest pressure to uniformly disperse the non-dry particulate, additives or coating stuffs into the material within the receptacle to produce a final product.

2. The method according to claim 1, wherein said non-dry particulate, additives or coating stuffs are added in a middle third region of the charging level of the material within the receptacle or into a mixing spout of material formed by rotation of said mixing tool in said receptacle.

3. The method according to claim 2, wherein the charging level of the material in the receptacle or the level of the mixing spout in the receptacle is maintained such that said level is always above the location of the feeding device.

4. The method according to claim 1, wherein said feeding device is formed by at least one opening or nozzle located in the lateral wall.

5. The method according to claim 4, wherein the feeding device is mounted flush with an inside of the lateral wall of the receptacle.

6. The method according to claim 1, wherein said feeding device comprises at least one metering pump.

7. The method according to claim 6, wherein said metering pump is a gear pump or diaphragm pump.

8. The method according to claim 6, wherein the at least one metering pump is configured to meter said additives in the form of droplets.

9. The method according to claim 1, wherein the lateral wall of the receptacle is heated to reduce viscosity of the additives fed Into receptacle.

10. The method according to claim 1, wherein said additives are fed into the material in the receptacle in an amount of between 0.01 and 20% by weight with respect to a total weight of the final product.

11. The method according to claim 1, wherein said additives are fed into the material in the receptacle to thoroughly wet the material.

12. The method according to claim 1, wherein an inner surface of the receptacle is a non-wettable surface.

13. The method according to claim 12, wherein the non-wettable surface comprises an anti-adhesion coating or embossing.

14. The method according to claim 1, wherein said mixing tool is rotatable about a vertical axis.

15. The method according to claim 1, wherein the material is a plastic material in the form of non-molten polymeric particles, wood fibers, or scraps of paper.

16. The method according to claim 1, wherein the feeding device is configured to deliver the non-dry particulate, additives, or coating stuffs into the receptacle in a suspended or emulsified form.

17. The method according to claim 1, wherein the feeding device is configured to deliver the non-dry particulate, additives, or coating stuffs into the receptacle at an elevated viscosity.

18. The method according to claim 1, wherein the feeding device is configured to feed at least one member of the group consisting of: peroxides, fats, waxes, IV enhancers, and polymers into the material in the receptacle.

19. The method according to claim 1, wherein the feeding device does not protrude or project from the lateral wall of said receptacle towards an interior of said receptacle.

20. The method according to claim 1, further comprising providing a motor to rotate the mixing tool.

\* \* \* \* \*